United States Patent
Jung et al.

(10) Patent No.: US 12,400,345 B2
(45) Date of Patent: Aug. 26, 2025

(54) METHOD AND DEVICE FOR MATCHING THREE-DIMENSIONAL ORAL SCAN DATA VIA DEEP-LEARNING BASED 3D FEATURE DETECTION

(71) Applicant: HDX WILL CORP., Seoul (KR)

(72) Inventors: Hong Jung, Seoul (KR); Sung Min Lee, Bucheon-si (KR); Bo Hyun Song, Seoul (KR)

(73) Assignee: HDX WILL CORP., Seoul (KR)

( * ) Notice: Subject to any disclaimer, the term of this patent is extended or adjusted under 35 U.S.C. 154(b) by 224 days.

(21) Appl. No.: 18/261,433

(22) PCT Filed: Jan. 13, 2022

(86) PCT No.: PCT/KR2022/000653
§ 371 (c)(1),
(2) Date: Jul. 13, 2023

(87) PCT Pub. No.: WO2022/154523
PCT Pub. Date: Jul. 21, 2022

(65) Prior Publication Data
US 2024/0070882 A1    Feb. 29, 2024

(30) Foreign Application Priority Data

Jan. 18, 2021 (KR) ........................ 10-2021-0006549

(51) Int. Cl.
*G06T 7/33* (2017.01)
*A61C 9/00* (2006.01)
(Continued)

(52) U.S. Cl.
CPC .............. *G06T 7/33* (2017.01); *A61C 9/0046* (2013.01); *G06T 7/593* (2017.01); *G06T 11/00* (2013.01);
(Continued)

(58) Field of Classification Search
CPC . G06T 7/33; G06T 7/593; G06T 11/00; G06T 2200/04; G06T 2207/10012;
(Continued)

(56) References Cited

U.S. PATENT DOCUMENTS

2005/0089213 A1    4/2005  Geng
2006/0263739 A1*  11/2006  Sporbert .............. A61C 9/0053
                                                            433/213
(Continued)

FOREIGN PATENT DOCUMENTS

JP    2019162426 A    9/2019
KR    101911327 B1    10/2018
(Continued)

OTHER PUBLICATIONS

International Search Report issued in International application No. PCT/KR2022/000653 dated May 4, 2022 (3 pages).
Written Opinion issued in International application No. PCT/KR2022/000653 dated May 4, 2022 (4 pages).
Extended European Search Report issued in European Application No. 22739718.9, dated Nov. 18, 2024 (8 pages).

*Primary Examiner* — Maurice L. McDowell, Jr.
(74) *Attorney, Agent, or Firm* — Osha Bergman Watanabe & Burton LLP (57) ABSTRACT

Disclosed is a three-dimensional oral scan data matching device including a matching unit, a deep-learning unit, a scanned frame feature determination unit, and a scan data re-matching unit. The matching unit matches a plurality of scanned frames to generate a full mouth image. The deep-learning unit performs deep-learning to detect a feature of the full mouth image. The scanned frame feature determination unit determines a feature of the plurality of scanned frames by utilizing the feature of the full mouth image. The scan data re-matching unit re-matches the plurality of scanned frames on the basis of the feature of the plurality of scanned frames, to reconstruct a three-dimensional oral model.

13 Claims, 6 Drawing Sheets

(51) Int. Cl.
  *G06T 7/593* (2017.01)
  *G06T 11/00* (2006.01)
(52) U.S. Cl.
  CPC .............................. *G06T 2200/04* (2013.01);
      *G06T 2207/10012* (2013.01); *G06T 2207/20081* (2013.01); *G06T 2207/30036* (2013.01)
(58) Field of Classification Search
  CPC . G06T 2207/20081; G06T 2207/30036; G06T 17/00; A61C 9/0046; A61C 9/0053; A61B 5/0088; A61B 5/7264
  See application file for complete search history.

(56)   References Cited

U.S. PATENT DOCUMENTS

| | | | | |
|---|---|---|---|---|
| 2018/0028065 A1* | 2/2018 | Elbaz | .................. | H04N 13/221 |
| 2018/0028294 A1* | 2/2018 | Azernikov | ........ | G06F 18/24143 |
| 2020/0005552 A1* | 1/2020 | Furst | ....................... | G06T 7/344 |
| 2020/0085546 A1* | 3/2020 | Li | .......................... | A61C 7/08 |

FOREIGN PATENT DOCUMENTS

| | | |
|---|---|---|
| KR | 102056480 B1 | 1/2020 |
| KR | 20200100448 A | 8/2020 |
| KR | 20210000942 A | 1/2021 |
| KR | 102310662 B1 | 10/2021 |

\* cited by examiner

METHOD AND DEVICE FOR MATCHING THREE-DIMENSIONAL ORAL SCAN DATA VIA DEEP-LEARNING BASED 3D FEATURE DETECTION

TECHNICAL FIELD

The present invention relates to a method and device for matching three-dimensional (3D) intraoral scan data through deep learning-based 3D feature point detection.

BACKGROUND ART

In order to generate three-dimensional (3D) intraoral scan data from an intraoral scanner, a process of scanning an oral cavity of a patient with a scanner and matching (registration) point clouds generated for each frame into one frame in three dimensions is required. There is an iterative closest point (ICP) algorithm that is widely used for matching of point clouds. In the existing method, even when a matching error between frames of one frame pair is small, geometric distortion occurs in a finally reconstructed 3D oral cavity model due to accumulated errors.

RELATED ART DOCUMENT

Patent Document (Patent Document 1) Korean Patent Registration No. 10-1911327

DISCLOSURE

Technical Problem

The present invention is directed to providing a method and device for matching three-dimensional (3D) intraoral scan data that can reduce geometric distortion.

Technical Solution

One aspect of the present invention provides a method of matching three-dimensional (3D) intraoral scan data, which includes matching a plurality of scanned frames and generating a full mouth image; detecting feature points of the full mouth image by performing deep learning; determining feature points of the plurality of scanned frames using the feature points of the full mouth image; and re-matching the plurality of scanned frames on the basis of the feature points of the plurality of scanned frames and reconstructing a 3D oral cavity model.

The determining of the feature points of the plurality of scanned frames using the feature points of the full mouth image may include generating a virtual frame from the full mouth image, projecting the feature points of the full mouth image onto the virtual frame and determining feature points of the virtual frame, and determining the feature points of the plurality of scanned frames using the feature points of the virtual frame.

The determining of the feature points of the plurality of scanned frames using the feature points of the virtual frame may include generating a first patch image having a predetermined size around a feature point of the virtual frame, selecting a second patch image within a scanned frame corresponding to the virtual frame on the basis of the first patch image, and determining a center point of the second patch image as a feature point of the scanned frame corresponding to the virtual frame.

A similarity between the first patch image and the second patch image may be greater than a threshold value.

The virtual frame may be generated from the full mouth image on the basis of an orientation and size of the scanned frame.

The reconstructing of the 3D oral cavity model may include matching the feature points of the plurality of scanned frames and determining a matching pair, and re-matching the plurality of scanned frames on the basis of the matching pair and reconstructing the 3D oral cavity model.

The plurality of scan frames may be matched using an iterative closest point (ICP) algorithm.

The detecting of the feature points of the full mouth image may include generating a rendered two-dimensional (2D) image by rendering the full mouth image, and detecting the feature points of the full mouth image by applying deep learning to the rendered 2D image.

The detecting of the feature points of the full mouth image by applying the deep learning to the rendered 2D image may include generating a heatmap for points where teeth meet by applying deep learning to the rendered 2D image, and detecting the feature points of the full mouth image from the heatmap.

The detecting of the feature points of the full mouth image by applying the deep learning to the rendered 2D image may further include when a first tooth meets a second tooth at a first feature point and the second tooth meets a third tooth at a second feature point, determining a center point between the first feature point and the second feature point, determining three straight lines passing through the first point, the second point, and the center point while being perpendicular to a straight line passing through the first feature point and the second feature point, and determining additional feature points, other than the first point and the second point, on the three straight lines.

Another aspect of the present invention provides a device for matching 3D intraoral scan data, which includes a matching unit configured to match a plurality of scanned frames to generate a full mouth image; a deep learning unit configured to detect feature points of the full mouth image by performing deep learning; a scanned frame feature point determination unit configured to determine feature points of the plurality of scanned frames using the feature points of the full mouth image; and a scan data re-matching unit configured to re-match the plurality of scanned frames on the basis of the feature points of the plurality of scanned frames to reconstruct a 3D oral cavity model.

The device for matching the 3D intraoral scan data may further include a virtual frame generation unit configured to generate a virtual frame from the full mouth image; and a virtual frame feature point determination unit configured to project the feature points of the full mouth image onto the virtual frame to determine feature points of the virtual frame, wherein the scanned frame feature point determination unit may determine the feature points of the plurality of scanned frames using the feature points of the virtual frame.

The device for matching the 3D intraoral scan data may further include a feature point matching unit configured to match the feature points of the plurality of scanned frames to determine a matching pair, wherein the scan data re-matching unit may re-match the plurality of scanned frames on the basis of the matching pair to reconstruct the 3D oral cavity model.

Advantageous Effects

According to the embodiment of the present invention, by obtaining a matching pair between frame models using deep learning and re-matching scanned frames on the basis of the matching pair, it is possible to reduce an overall matching error of a reconstructed scan model.

MODES OF THE INVENTION

Hereinafter, embodiments of the present invention that can be easily performed by those skilled in the art will be described in detail with reference to the accompanying drawings. In addition, parts irrelevant to description are omitted in the drawings in order to clearly explain the present invention.

Figure 1:
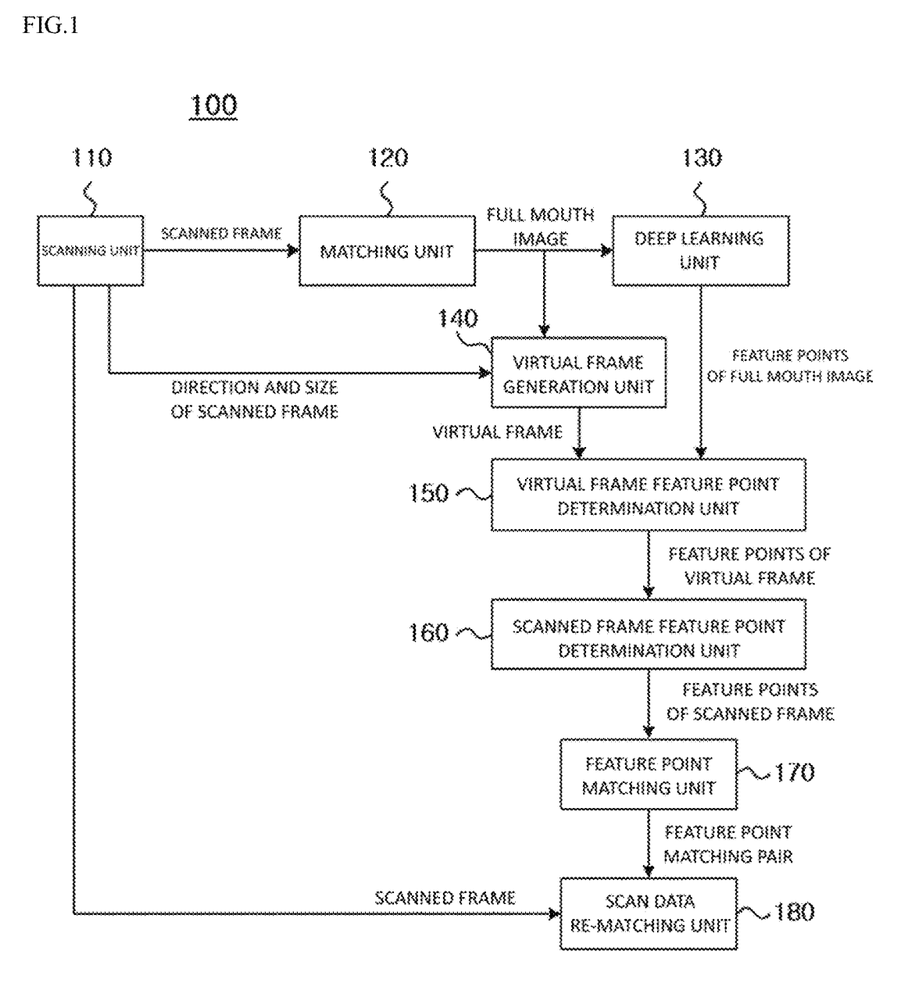
FIG. 1 is a block diagram of a device for matching three-dimensional (3D) intraoral scan data according to an embodiment of the present invention.

FIG. 1 is a block diagram of a device for matching three-dimensional (3D) intraoral scan data according to an embodiment of the present invention.

As shown in FIG. 1, a device 100 for matching 3D intraoral scan data according to the embodiment of the present invention includes a scanning unit 110, a matching unit 120, a deep learning unit 130, a virtual frame generation unit 140, a virtual frame feature point determination unit 150, a scanned frame feature point determination unit 160, a feature point matching unit 170, and a scan data re-matching unit 180. The operation of each component of the device 100 for matching 3D intraoral scan data will be described below.

Figure 2:
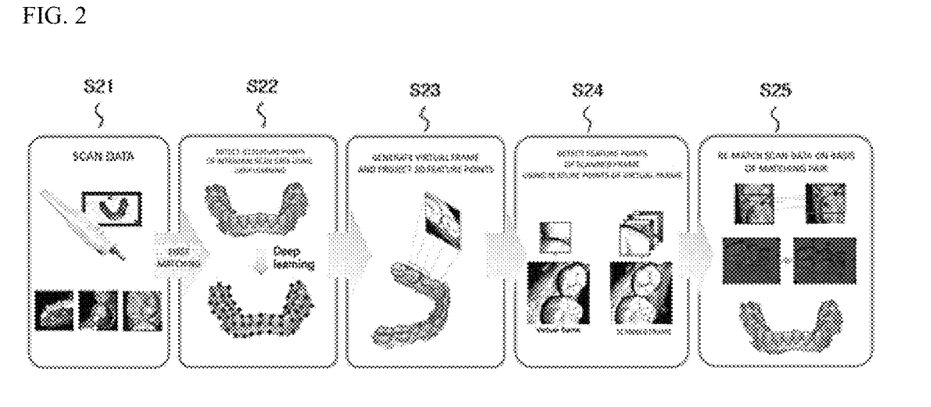
FIG. 2 schematically shows an operating method of a device for matching 3D intraoral scan data according to an embodiment of the present invention.

FIG. 2 schematically shows an operating method of the device for matching the 3D intraoral scan data according to the embodiment of the present invention.

In particular, FIG. 2 shows a 3D oral cavity model reconstruction process for reducing matching errors accumulated during a process of reconstructing intraoral scan data.

As shown in FIG. 2, the scanning unit 110 scans an oral cavity to generate a plurality of scanned frames (S21).

The matching unit 120 generates a full mouth image by matching the plurality of scanned frames using an iterative closest point (ICP) algorithm, and the deep learning unit 130 determines 3D feature points in the full mouth image by performing deep learning (S22).

The virtual frame generation unit 140 generates a virtual frame from the full mouth image on the basis of an orientation and size of the scanned frames, and the virtual frame feature point determination unit 150 projects the feature points of the full mouth image onto the virtual frame to determine feature points of the virtual frame (S23).

The scanned frame feature point determination unit 160 determines feature points of the plurality of scanned frames using the feature points of the virtual frame (S24).

The feature point matching unit 170 matches the feature points of the plurality of scanned frames to determine a matching pair, and the scan data re-matching unit 180 re-matches the plurality of scanned frames on the basis of the matching pair to reconstruct the 3D oral cavity model (S25).

Figure 3:
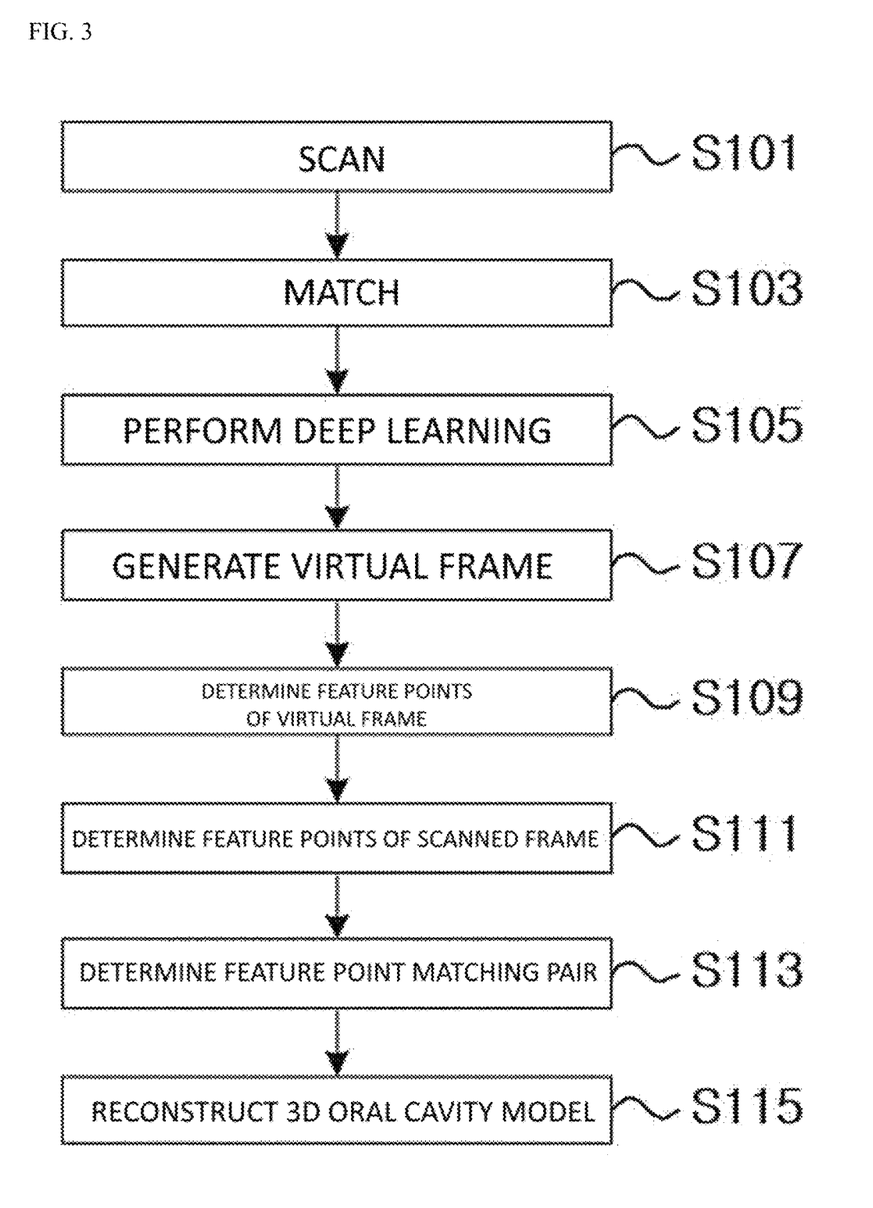
FIG. 3 is a flowchart illustrating an operating method of a device for matching 3D intraoral scan data according to an embodiment of the present invention.

FIG. 3 is a flowchart illustrating an operating method of a device for matching 3D intraoral scan data according to an embodiment of the present invention.

The scanning unit 110 scans an oral cavity to generate a plurality of scanned frames (S101).

The matching unit 120 matches the plurality of scanned frames using, for example, an ICP algorithm to generate a full mouth image (S103). The matching method includes any method of obtaining rigid-body transformations through iterative surface matching, such as ICP.

Next, an oral cavity scan and scan image matching process will be described with reference to FIG. 4.

Figure 4:
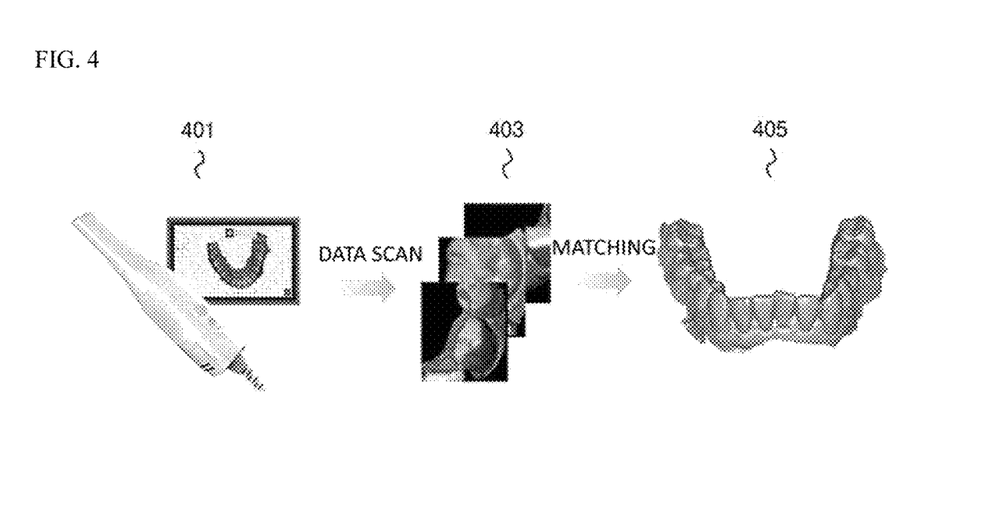
FIG. 4 shows an oral cavity scan and scan image matching process according to an embodiment of the present invention.

FIG. 4 shows an oral cavity scan and scan image matching process according to an embodiment of the present invention.

As shown in FIG. 4, the scanning unit 110 may scan an oral cavity 401 to generate a plurality of scanned frames 403, and the matching unit 120 may match the plurality of scanned frames to generate a full mouth image 405.

Again, FIG. 3 will be described.

The deep learning unit 130 detects 3D feature points in the full mouth image by performing deep learning (S105). Since handling 3D mesh data directly in the deep learning process may have a problem of high computational cost, the deep learning unit 130 may generate a rendered two-dimensional (2D) image by rendering the full mouth image instead of 3D scan data, and apply deep learning to the 2D image.

For data learning, the deep learning unit 130 may use a 2D image rendered in a z-direction of the full mouth image, which is full mouth scan data, as an input of deep learning and use adjacent 2D points between teeth as an output of deep learning. In consideration of the fact that patients have different numbers of teeth, the deep learning unit 130 does not use a coordinate vector of a constant number of feature points as an output of deep learning, but may generate a heatmap image that displays the positions of feature points and use the heatmap image as an output of deep learning to train a deep learning network. The heatmap is a data visualization technique that shows the intensity of a phenomenon as color in two dimensions. Therefore, the deep learning unit 130 may perform deep learning and output a heatmap that shows the intensity of feature points as color. In order to obtain 3D feature points from a 2D heatmap, the deep learning unit 130 may retrieve 2D coordinates of points having the maximum intensity in the heatmap and project the points onto a 3D full mouth image to obtain 3D feature points of the 3D full mouth image.

Next, a process of obtaining feature points of a 3D full mouth image will be described with reference to FIGS. 5 and 6.

Figure 5:
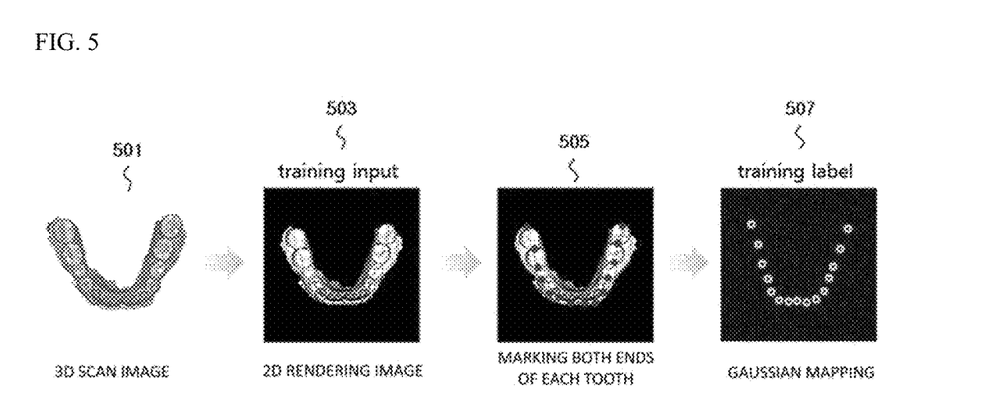
FIG. 5 shows a process of generating a heatmap according to an embodiment of the present invention.

FIG. 5 shows a process of generating a heatmap according to an embodiment of the present invention.

As shown in FIG. 5, the deep learning unit 130 generates a 2D rendered image 503 by rendering a 3D full mouth image 501. The deep learning unit 130 may determine a point where teeth meet in the 2D rendered image 503 (505), and generate a heatmap 507 by performing Gaussian mapping on the determined point.

Figure 6:
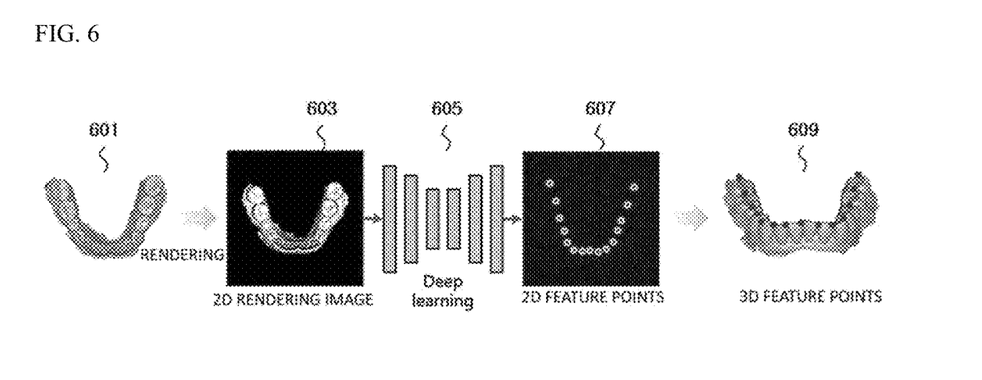
FIG. 6 shows a process of determining 3D feature points of a full mouth image according to an embodiment of the present invention.

FIG. 6 shows a process of determining 3D feature points of a full mouth image according to an embodiment of the present invention.

As shown in FIG. 6, the deep learning unit 130 generates a 2D rendered image 603 by rendering a 3D full mouth image 601. The deep learning unit 130 performs deep learning 605 using the 2D rendered image 603 as an input to generate a heatmap 607 for a point where teeth meet. The deep learning unit 130 may determine 3D feature points 609 of a full mouth image on the basis of the heatmap 607.

Since at least three feature points are required for each frame to match a plurality of scanned frames, more points are additionally required in addition to adjacent points between teeth. A process of obtaining additional feature points in addition to adjacent points between teeth will be described with reference to FIG. 7.

Figure 7:
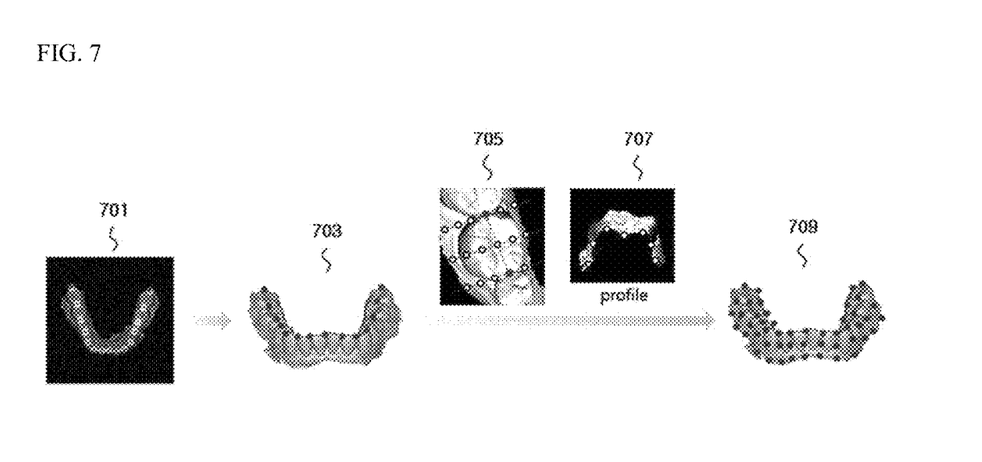
FIG. 7 shows a process of additionally determining 3D feature points of a full mouth image according to an embodiment of the present invention.

FIG. 7 shows a process of additionally determining 3D feature points of a full mouth image according to an embodiment of the present invention.

The deep learning unit 130 may determine 3D feature points 703 of a full mouth image on the basis of a heatmap 701.

When it is assumed that a first tooth meets a second tooth at a first point and the second tooth meets a third tooth at a second point, the deep learning unit 130 determines a center point between the first point and the second point, and the deep learning unit 130 determines three straight lines passing through the first point, the second point, and the center point while being perpendicular to a straight line passing through the first point and the second point (705). The deep learning unit 130 may determine additional feature points, other than the first point and the second point, on the three straight lines (707).

By applying the above process to all the teeth, the deep learning unit 130 may determine at least three times as many feature points as the number of teeth for the entirety of the full mouth image (709).

Again, FIG. 3 will be described.

The virtual frame generation unit 140 generates a virtual frame from the full mouth image on the basis of an orientation and size of the scanned frames (S107). The virtual frame generation unit 140 may generate the virtual frame by rendering the full mouth image in the same orientation and the same size as the scanned frames. The virtual frame may represent a rendered image, a depth map, or both the rendered image and the depth map.

The virtual frame feature point determination unit 150 projects the feature points of the full mouth image onto the virtual frame to determine feature points of the virtual frame (S109).

Figure 8:
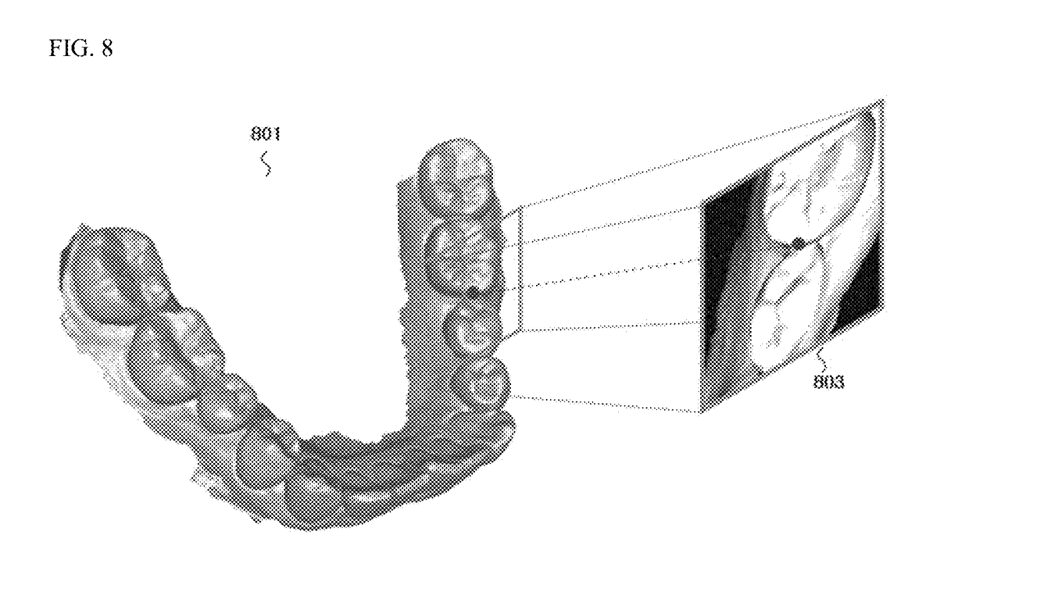
FIG. 8 shows a process of determining feature points of a virtual frame according to an embodiment of the present invention.

FIG. 8 shows a process of determining feature points of a virtual frame according to an embodiment of the present invention.

As shown in FIG. 8, the virtual frame feature point determination unit 150 may project feature points of a full mouth image 801 onto a virtual frame 803 to determine feature points of the virtual frame 803.

The scanned frame feature point determination unit 160 determines feature points of a plurality of scanned frames using the feature points of the virtual frame (S111). Specifically, the scanned frame feature point determination unit 160 may generate a patch image having a predetermined size around a feature point of the virtual frame. The scanned frame feature point determination unit 160 may select a patch image having a similarity with the patch image greater than a threshold value from the scanned frame. The scanned frame feature point determination unit 160 may determine a center point of the patch image selected from the scanned frame as a feature point of the scanned frame.

Figure 9:
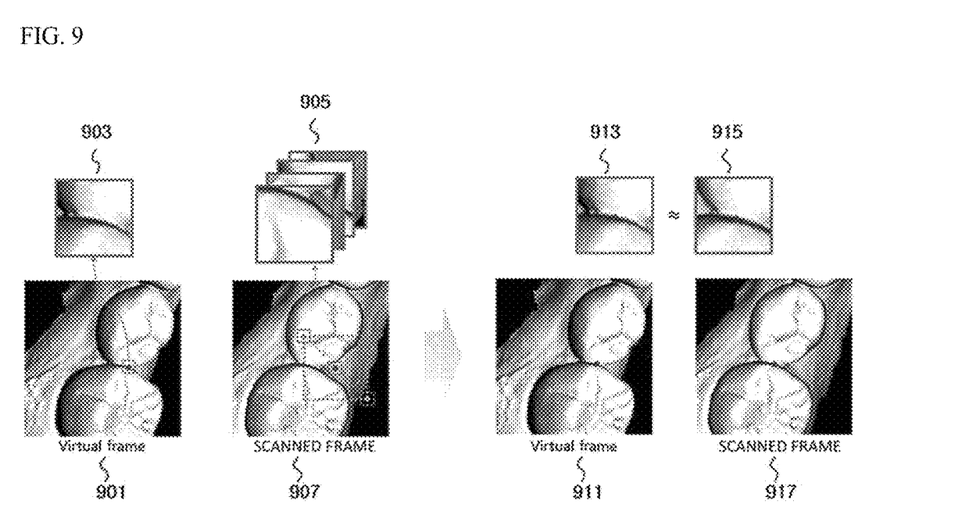
FIG. 9 shows a process of determining feature points of a plurality of scanned frames according to an embodiment of the present invention.

FIG. 9 shows a process of determining feature points of a plurality of scanned frames according to an embodiment of the present invention.

The scanned frame feature point determination unit 160 may generate a patch image 903 having a predetermined size around a feature point of a virtual frame 901. The scanned frame feature point determination unit 160 may select a patch image 905 having a similarity with the patch image 903 greater than a threshold value from a scanned frame 907. However, when searching for a patch image similar to the patch image 903 in the entire scanned frame 907, two or more patch images 905 may be selected as shown in FIG. 9, or unwanted patch images 905 having a large error may be selected.

In order to solve the above problem, first, the scanned frame feature point determination unit 160 may generate a patch image 913 having a predetermined size around a feature point of a virtual frame 911. The scanned frame feature point determination unit 160 may select a patch image 915 having a similarity with the patch image 913 greater than a threshold value from an area of a scanned frame 917 corresponding to the vicinity of a feature point of the virtual frame 911. Thereafter, the scanned frame feature point determination unit 160 may determine a center point of the patch image selected from the scanned frame as a feature point of the scanned frame, thereby reducing the amount of calculation and error.

Again, FIG. 3 will be described.

The feature point matching unit 170 determines a matching pair by matching the feature points of the plurality of scanned frames (S113).

The scan data re-matching unit 180 reconstructs a 3D oral cavity model by re-matching the plurality of scanned frames on the basis of the matching pair (S115). A process of reconstructing the 3D oral cavity model will be described with reference to FIGS. 10 and 11.

Figure 10:
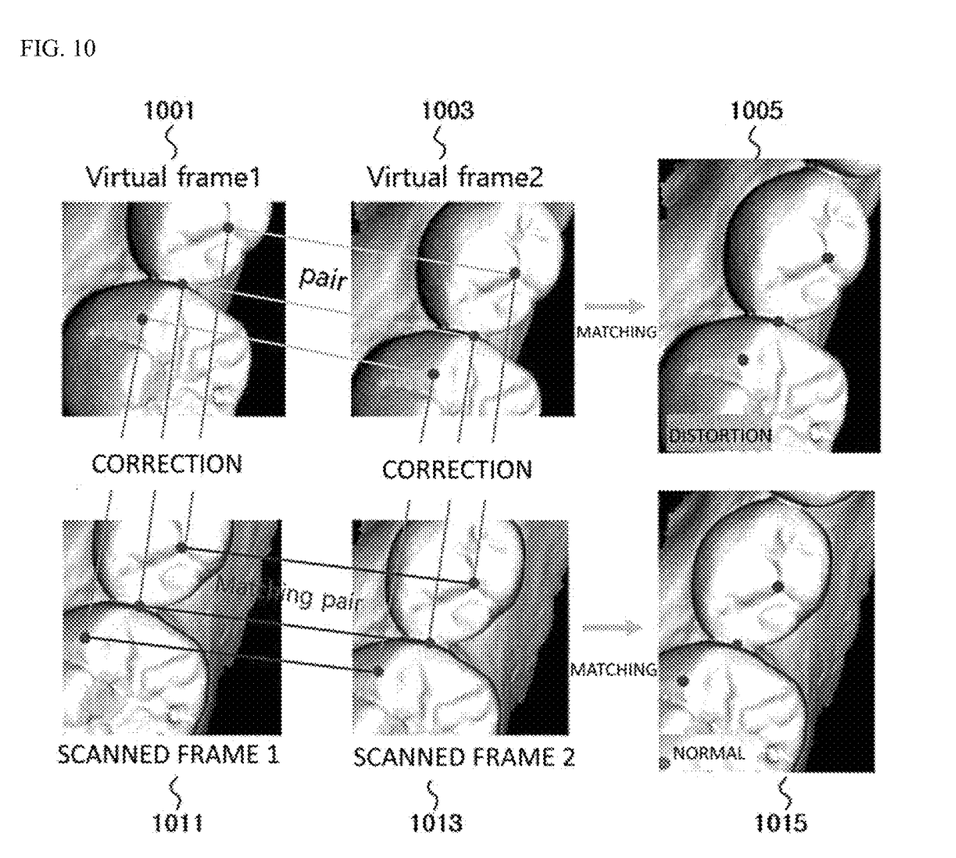
FIG. 10 shows a process of reconstructing a 3D oral cavity model according to an embodiment of the present invention.

FIG. 10 shows a process of reconstructing a 3D oral cavity model according to an embodiment of the present invention.

As shown in FIG. 10, since there are differences between virtual frames and scanned frames due to errors generated in the matching process of the matching unit 120, when a first virtual frame 1001 and a second virtual frame 1003 are matched based on a feature point pair between the first virtual frame 1001 and the second virtual frame 1003, spatial distortion may occur in a matched image 1005.

However, when feature points of the first virtual frame 1001 and second virtual frame 1003 are transferred to a first scanned frame 1011 and a second scanned frame 1013, and the first scanned frame 1011 and the second scanned frame 1013 are matched based on a feature point pair between the first scanned frame 1011 and the second scanned frame 1013, a matched image 1015 may have reduced spatial distortion.

Figure 11:
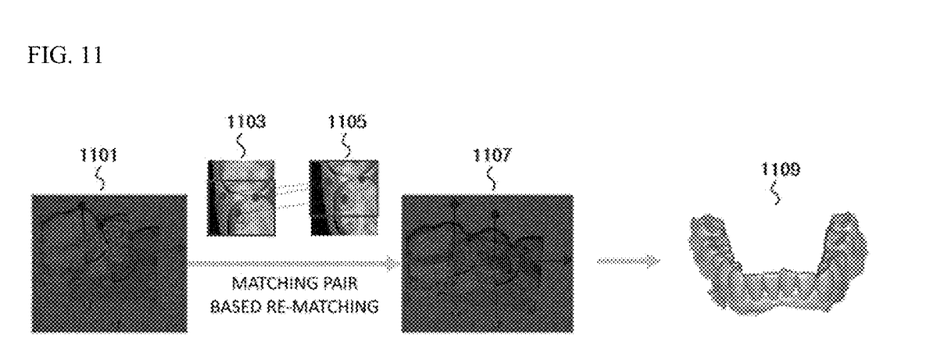
FIG. 11 shows a process of reconstructing a 3D oral cavity model according to another embodiment of the present invention.

FIG. 11 shows a process of reconstructing a 3D oral cavity model according to another embodiment of the present invention.

As shown in FIG. 11, an oral cavity image 1101 generated by the matching unit 120 has spatial distortion. It can be seen that, since the scan data re-matching unit 180 generates a matched image 1107 by re-matching a plurality of scanned frames 1103 and 1105 on the basis of a feature point matching pair, spatial distortion is reduced. As a result, a 3D oral cavity model 1109 generated from the image 1107 with little spatial distortion also has little spatial distortion.

While the present invention has been described with reference to the embodiment illustrated in the accompanying drawings, the embodiment should be considered in a descriptive sense only, and it should be understood by those skilled in the art that various alterations and equivalent other embodiments may be made. Therefore, the scope of the present invention should be defined by only the following claims.

The invention claimed is:

1. A method of matching three-dimensional (3D) intraoral scan data, comprising:
    matching a plurality of scanned frames and generating a full mouth image;
    detecting feature points of the full mouth image by performing deep learning;
    determining feature points of the plurality of scanned frames using the feature points of the full mouth image; and
    re-matching the plurality of scanned frames on the basis of the feature points of the plurality of scanned frames and reconstructing a 3D oral cavity model.

2. The method of claim 1, wherein the determining of the feature points of the plurality of scanned frames using the feature points of the full mouth image includes:
    generating a virtual frame from the full mouth image;
    projecting the feature points of the full mouth image onto the virtual frame and determining feature points of the virtual frame; and
    determining the feature points of the plurality of scanned frames using the feature points of the virtual frame.

3. The method of claim 2, wherein the determining of the feature points of the plurality of scanned frames using the feature points of the virtual frame includes:
    generating a first patch image having a predetermined size around a feature point of the virtual frame;
    selecting a second patch image within a scanned frame corresponding to the virtual frame on the basis of the first patch image; and
    determining a center point of the second patch image as a feature point of the scanned frame corresponding to the virtual frame.

4. The method of claim 3, wherein a similarity between the first patch image and the second patch image is greater than a threshold value.

5. The method of claim 2, wherein the virtual frame is generated from the full mouth image on the basis of an orientation and size of the scanned frame.

6. The method of claim 1, wherein the reconstructing of the 3D oral cavity model includes:
    matching the feature points of the plurality of scanned frames and determining a matching pair; and
    re-matching the plurality of scanned frames on the basis of the matching pair and reconstructing the 3D oral cavity model.

7. The method of claim 1, wherein the plurality of scanned frames are matched using an iterative closest point (ICP) algorithm.

8. The method of claim 1, wherein the detecting of the feature points of the full mouth image includes:
    generating a rendered two-dimensional (2D) image by rendering the full mouth image; and
    detecting the feature points of the full mouth image by applying deep learning to the rendered 2D image.

9. The method of claim 8, wherein the detecting of the feature points of the full mouth image by applying the deep learning to the rendered 2D image includes:
    generating a heatmap for points where teeth meet by applying deep learning to the rendered 2D image; and
    detecting the feature points of the full mouth image from the heatmap.

10. The method of claim 8, wherein the detecting of the feature points of the full mouth image by applying the deep learning to the rendered 2D image further includes:
    when a first tooth meets a second tooth at a first feature point and the second tooth meets a third tooth at a second feature point, determining a center point between the first feature point and the second feature point;
    determining three straight lines passing through the first point, the second point, and the center point while being perpendicular to a straight line passing through the first feature point and the second feature point; and
    determining additional feature points, other than the first point and the second point, on the three straight lines.

11. A device for matching three-dimensional (3D) intraoral scan data, comprising:
    a matching unit configured to match a plurality of scanned frames to generate a full mouth image;
    a deep learning unit configured to detect feature points of the full mouth image by performing deep learning;
    a scanned frame feature point determination unit configured to determine feature points of the plurality of scanned frames using the feature points of the full mouth image; and
    a scan data re-matching unit configured to re-match the plurality of scanned frames on the basis of the feature points of the plurality of scanned frames to reconstruct a 3D oral cavity model.

12. The device of claim 11, further comprising:
    a virtual frame generation unit configured to generate a virtual frame from the full mouth image; and
    a virtual frame feature point determination unit configured to project the feature points of the full mouth image onto the virtual frame to determine feature points of the virtual frame,
    wherein the scanned frame feature point determination unit determines the feature points of the plurality of scanned frames using the feature points of the virtual frame.

13. The device of claim 11, further comprising a feature point matching unit configured to match the feature points of the plurality of scanned frames to determine a matching pair,
    wherein the scan data re-matching unit re-matches the plurality of scanned frames on the basis of the matching pair to reconstruct the 3D oral cavity model.

* * * * *